United States Patent
Yum (10) Patent No.: US 11,244,771 B2
(45) Date of Patent: Feb. 8, 2022

(54) COMPOSITION FOR CONVERTING RADIOACTIVE SUBSTANCE INTO NON-RADIOACTIVE SUBSTANCE AND A METHOD OF PREPARING THE COMPOSITION

(71) Applicant: COENBIO CO., LTD., Seongnam-Si (KR)

(72) Inventor: Kyu Jin Yum, Anyang-si (KR)

(73) Assignee: COENBIO CO., LTD., Seongnam-Si (KR)

( * ) Notice: Subject to any disclaimer, the term of this patent is extended or adjusted under 35 U.S.C. 154(b) by 168 days.

(21) Appl. No.: 16/488,377

(22) PCT Filed: Jul. 9, 2019

(86) PCT No.: PCT/KR2019/008451
§ 371 (c)(1),
(2) Date: Aug. 23, 2019

(87) PCT Pub. No.: WO2021/006380
PCT Pub. Date: Jan. 14, 2021

(65) Prior Publication Data
US 2021/0012916 A1    Jan. 14, 2021

(51) Int. Cl.
| | | |
|---|---|---|
| G21F 9/00 | (2006.01) | |
| G21G 7/00 | (2009.01) | |
| G21F 9/04 | (2006.01) | |
| G21F 9/28 | (2006.01) | |

(52) U.S. Cl.
CPC . *G21F 9/04* (2013.01); *G21F 9/28* (2013.01)

(58) Field of Classification Search
CPC . B09B 5/00; G21G 7/00; C12N 1/185; C12N 1/20; C12N 1/205; C12N 1/16; G21F 9/28; G21F 9/18; G21F 9/04; C12R 2001/85; C12R 2001/07; B09C 1/105
See application file for complete search history.

(56) References Cited

U.S. PATENT DOCUMENTS

| | | | |
|---|---|---|---|
| 2004/0107473 A1* | 6/2004 | Jones et al. | 2/69 |
| 2010/0285559 A1* | 11/2010 | Dassharma et al. | 435/173.9 |
| 2013/0078707 A1* | 3/2013 | Rivasseau et al. | 435/257.1 |

FOREIGN PATENT DOCUMENTS

| | | | | |
|---|---|---|---|---|
| JP | 58-45918 B2 | 10/1983 | | |
| JP | 04243600 A | * 8/1992 | | C02F 3/34 |
| JP | 2005-321365 A | 11/2005 | | |
| JP | 2006-517097 A | 7/2006 | | |
| JP | 2013-122427 A | 6/2013 | | |
| JP | 2013-130574 A | 7/2013 | | |
| JP | 2013-174557 A | 9/2013 | | |
| JP | 2013-217820 A | 10/2013 | | |
| JP | 2014-032167 A | 2/2014 | | |
| JP | 2014-169919 A | 9/2014 | | |
| JP | 2015-78970 A | 4/2015 | | |
| KR | 10-2015-0077575 A | 7/2015 | | |
| KR | 10-1754790 B1 | 7/2017 | | |
| KR | 10-2020-0005048 A | 1/2020 | | |

OTHER PUBLICATIONS

Goto Kunio., JP 2014032167 A (2014), "Radioactive Decontaminant and Manufacturing Method for the Same", A machine Translation provided by PTO-STIC services (total pp. 1-10). (Year: 2014).*

Toya et al., JP 04243600 A (1992), "Treating of Organic Polluted Water With Photosynthetic Microorganism", A Machine Translation provided by PTO-STIC services (total pp. 1-7). (Year: 1992).*

* cited by examiner

*Primary Examiner* — Satyendra K Singh
(74) *Attorney, Agent, or Firm* — Seed IP Law Group LLP (57) ABSTRACT

The present invention relates to a composition for transmuting a radioactive substance into a non-radioactive substance using complex microorganisms and a method for preparing the composition.

9 Claims, 7 Drawing Sheets

D1: Composition 1 of Example 2 comprising microorganisms + cesium

D2: Composition 2 of Example 2 comprising microorganisms + cesium

[FIG. 4]

DX1: Composition 1 of Example 1 comprising microorganisms + cesium

DX2: Composition 2 of Example 1 comprising microorganisms + cesium

[FIG. 5]

D1: Composition 1 of Example 2 comprising microorganisms + cesium
D2: Composition 2 of Example 2 comprising microorganisms + cesium
DX1: Composition 1 of Example 1 comprising microorganisms + cesium
DX2: Composition 2 of Example 1 comprising microorganisms + cesium

MRS: de Man, Rogosa & Sharpe media
TSA: Tryptic Soy Agar
NA: Nutrient Agar
PDA: Potato Dextrose Agar

COMPOSITION FOR CONVERTING RADIOACTIVE SUBSTANCE INTO NON-RADIOACTIVE SUBSTANCE AND A METHOD OF PREPARING THE COMPOSITION

TECHNICAL FIELD

The present invention relates to a composition for transmuting a radioactive substance into a non-radioactive substance using complex microorganisms and a method for preparing the composition.

BACKGROUND ART

A fundamental solution to safe disposal of spent nuclear fuel as high-level radioactive nuclear waste as well as intermediate-level and low-level radioactive waste from nuclear power plants is a prerequisite for continuous utilization of nuclear power plants as large-scale energy sources. Despite this situation, a satisfactory fundamental solution to the disposal of radioactive waste has not been proposed so far. Long-term storage in safe places is accepted as the only way to dispose of radioactive waste.

However, radioactive waste disposal facilities do not provide a fundamental solution to radioactive waste disposal due to their limited storage capacity. No approach can be considered as a fundamental solution to nuclear waste disposal as long as radioactive substances remain untransmuted while emitting radioactive rays.

A fundamental solution to this situation is required to drastically reduce radioactive waste. For example, techniques for transmuting Cs-137 as a radionuclide into safe, non-radioactive elements Ba-137 or Ba-138 can be considered. However, no satisfactory techniques have yet been put to practical use.

Transmutation of radionuclides is observed mainly in radioactive substances with high atomic number. According to recent studies on cold nuclear fusion, transmutation with very low energy input at room temperature is observed. This phenomenon is not described by current nuclear physics theories. In the academic literature, transmutation is represented by neologisms such as "low energy nuclear reaction (LENR)", "lattice assisted nuclear reaction (LANR)", "condensed matter nuclear science (CMNS)", and "chemically assisted nuclear reaction (CANR)", which are used to distinguish transmutation from conventional nuclear reactions.

In connection with radioactive waste disposal using microorganisms, several techniques have been reported in South Korea. For example, Korean Patent No. 10-1754790 discloses the use of microorganisms for the capture of radioactive substances to prevent groundwater from being contaminated by the diffusion of radioactive substances. The purpose of this technique is to transmute a radioactive substance (cesium ion) into a sparingly water soluble substance (pautovite) to prevent the diffusion of contamination. However, this technique fails to transmute a radioactive substance into a safe element and cannot fundamentally reduce the risk of radioactive contamination.

Thus, successful transmutation of radioactive elements in radioactive waste into safe elements can provide a fundamental solution to radioactive waste disposal.

DISCLOSURE

Technical Problem

It is an aspect of the present invention to provide a composition for transmuting a radioactive substance into a non-radioactive substance comprising complex microorganisms.

It is another aspect of the present invention to provide a method for preparing a composition for transmuting a radioactive substance into a non-radioactive substance.

It is a further aspect of the present invention to provide a method for transmuting a radioactive substance into a non-radioactive substance, comprising bringing the composition described herein into contact with a radioactive substance.

Technical Solution

One aspect of the present invention relates to a composition for transmuting a radioactive substance into a non-radioactive substance comprising complex microorganisms.

The complex microorganisms may include two or more species selected from the group consisting of radiation-resistant microorganisms, yeast, fungi, photosynthetic bacteria, and green algae. As an example, the complex microorganisms may include at least three, more specifically at least four species selected from the group consisting of radiation-resistant microorganisms, yeast, fungi, photosynthetic bacteria, and green algae. The complex microorganisms include a radiation-resistant microorganism, yeast, a fungus, a photosynthetic bacterial species, and a green alga, which is preferred in terms of transmutation efficiency. As a further example, the complex microorganisms essentially include a radiation-resistant microorganism and a photosynthetic bacterial species and may optionally further include at least one species selected from the group consisting of yeast, fungi, and green algae. As another example, the complex microorganisms essentially include a radiation-resistant microorganism, a photosynthetic bacterial species, and yeast and may optionally further include at least one species selected from the group consisting of fungi and green algae. As another example, the complex microorganisms essentially include a radiation-resistant microorganism, a photosynthetic bacterial species, and a fungus and may optionally further include at least one species selected from the group consisting of yeast and green algae. As another example, the complex microorganisms essentially include a radiation-resistant microorganism, a photosynthetic bacterial species, and a green alga and may optionally further include at least one species selected from the group consisting of fungi and yeast. In the present invention, it was found that the microorganisms have no ability to transmute a radioactive substance into a non-radioactive substance when used alone but have the ability to transmute a radioactive substance into a non-radioactive substance when used in combination.

Any radiation-resistant microorganism that can survive even in the presence of radioactive substances may be used in the present invention. The radiation-resistant microorganism may be, for example, *Deinococcus* sp., *Cryptococcus* sp. or *Bacillus* sp. Specifically, the radiation-resistant microorganism may be *Deinococcus radiodurans*, *Bacillus safensis* or *Bacillus pumilus* but is not limited thereto. As an example, the radiation-resistant microorganism may be a *Bacillus safensis* strain (KCCM12163P) or a *Bacillus pumilus* strain (KCCM12165P). The two strains were deposited with the Korean Culture Center of Microorganisms (120-861, Hongje-2ga-Gil, Seodaemun-Ku, Seoul, Korea) on Nov. 10, 2017, respectively.

Any yeast that has antioxidant activity may be used in the present invention. The yeast may be, for example, *Cryptococcus* sp., *Saccharomyces* sp. or *Trichosporon* sp. Specifically, the yeast may be *Saccharomyces boulardii*, *Saccharomyces servazzii*, *Saccharomyces cerevisiae*, *Trichosporon cutaneum* and/or *Trichosporon loubieri* but is not limited thereto. As an example, the yeast may be a *Saccharomyces*

*servazzii* strain (KCCM12157P) and/or a *Trichosporon loubieri* strain (KCTC10876BP). The *Trichosporon loubieri* strain (KCTC10876BP) is known from U.S. Pat. No. 8,034,605B2, the entire disclosure of which is hereby incorporated by reference. The *Saccharomyces servazzii* strain (KCCM12157P) was deposited with the Korean Culture Center of Microorganisms (120-861, Hongje-2ga-Gil, Seodaemun-Ku, Seoul, Korea) on Nov. 10, 2017.

Any fungus that has antioxidant activity may be used in the present invention. The fungus may be, for example, *Irpex* sp. or *Phanerochaete* sp. Specifically, the fungus may be *Irpex lacteus, Irpex hydnoides, Phanerochaete chrysosporium* or *Phanerochaete sordida* but is not limited thereto. The *Phanerochaete chrysosporium* strain (KCCM10725P) is known from Korean Patent No. 10-0903666, the entire disclosure of which is hereby incorporated by reference.

Any photosynthetic bacterial species that can use light energy to assimilate carbon dioxide may be used in the present invention. The photosynthetic bacterial species may be, for example, *Rhodobacter* sp., *Chlorobium* sp., *Chromatium* sp., *Rhodospirillum* sp., or *Rhodopseudomonas* sp. More specifically, the photosynthetic bacterial species may be *Rhodobacter sphaeroides* or *Rhodobacter capsulatus* but is not limited thereto. Without being bound by theory, since the photosynthetic bacterial species uses protons ($H^+$) for carbon dioxide assimilation, the function of the photosynthetic bacterial species is assumed to play an important role in the ability of the complex microorganisms to transmute a radioactive substance into a non-radioactive substance.

Any green alga that has a green color due to the presence of chlorophyll may be used in the present invention. The green algae may be, for example, *Trebouxia* sp., *Stichococcus* sp., *Ehptochloris* sp. or *Coccomyxa* sp. Specifically, the green algae may be *Coccomyxa viridis* or *Stichococcus* sp. but is not limited thereto.

The complex microorganisms may be used in the form of culture broths including their respective cultures. The supernatants may be removed from the culture broths before use. Alternatively, the culture broths may be concentrated and mixed before use. The composition of each culture may further include not only one or more ingredients necessary for the culture of the corresponding microorganism but also one or more ingredients exerting a synergistic effect on the growth of the microorganism. The composition of each culture can be readily determined by those skilled in the art.

Each of the complex microorganisms may be present at a concentration of $0.5 \times 10^2$ CFU/ml to $2.5 \times 10^{10}$ CFU/ml, specifically $5 \times 10^3$ CFU/ml to $5 \times 10^{10}$ CFU/ml, more specifically $1 \times 10^5$ CFU/ml to $5 \times 10^9$ CFU/ml in the composition. The complex microorganisms may be present in a total amount of 0.05% by weight to 60% by weight, specifically 5% by weight to 50% by weight, more specifically 10% by weight to 40% by weight, based on the weight of the composition.

The radioactive substance refers to a substance capable of emitting radioactive rays such as $\alpha$, $\beta$ or $\gamma$-rays. For example, the radioactive substance may be cesium (Cs), uranium, iodine, strontium, iridium, radium or plutonium. In the present invention, it was found that the radioactive substance is transmuted into a non-radioactive substance by the complex microorganisms.

The weight ratio of the complex microorganisms to the radioactive substance may be from 9.9:0.1 to 0.1:9.9, specifically from 8:2 to 2:8, more specifically from 7:3 to 3:7.

The composition and/or the complex microorganisms may be in a liquid or dry state, specifically in the form of a dry powder.

The composition may further include an environmentally acceptable carrier. In this case, the composition may be formulated with the carrier to dispose of radioactive waste or to treat soil, groundwater and/or wastewater, contaminated with radioactive substances.

The term "environmentally acceptable carrier" as used herein refers to a carrier or diluent that causes no environmental damage and does not deteriorate the biological activity and properties of the complex microorganisms.

When formulated into a liquid solution, the acceptable carrier may be selected from saline solution, sterilized water, buffered saline, dextrose solution, maltodextrin solution, glycerol, and mixtures thereof that are suitable as nutrients for the complex microorganisms. If necessary, one or more general additives, such as antioxidants, buffer solutions, and bacteriostatic agents may be added to the composition. The composition of the present invention may be formulated into a liquid preparation such as an aqueous solution, suspension or emulsion or a solid preparation such as a powder. In this case, the composition of the present invention may further include one or more additives selected from diluents, dispersants, surfactants, binders, and lubricants. A binding agent, an emulsifier or a preservative may be further added to the composition to prevent the quality of the composition from deteriorating.

Another aspect of the present invention relates to a method for preparing a composition for transmuting a radioactive substance into a non-radioactive substance comprising complex microorganisms.

The complex microorganisms may include two or more species selected from the group consisting of radiation-resistant microorganisms, yeast, fungi, photosynthetic bacteria, and green algae. As an example, the complex microorganisms may include at least three, more specifically at least four species selected from the group consisting of radiation-resistant microorganisms, yeast, fungi, photosynthetic bacteria, and green algae. The complex microorganisms include a radiation-resistant microorganism, yeast, a fungus, a photosynthetic bacterial species, and a green alga, which is preferred in terms of transmutation efficiency. As a further example, the complex microorganisms essentially include a radiation-resistant microorganism and a photosynthetic bacterial species and may optionally further include at least one species selected from the group consisting of yeast, fungi, and green algae. As another example, the complex microorganisms essentially include a radiation-resistant microorganism, a photosynthetic bacterial species, and yeast and may optionally further include at least one species selected from the group consisting of fungi and green algae. As another example, the complex microorganisms essentially include a radiation-resistant microorganism, a photosynthetic bacterial species, and a fungus and may optionally further include at least one species selected from the group consisting of yeast and green algae. As another example, the complex microorganisms essentially include a radiation-resistant microorganism, a photosynthetic bacterial species, and a green alga and may optionally further include at least one species selected from the group consisting of fungi and yeast. Details of the complex microorganisms, the carrier, and the kinds and contents of the ingredients are the same as those described for the composition.

The method may include culturing complex microorganisms individually or at least partially together. The individual microorganisms can be cultured by suitable methods known in the art.

Natural or synthetic media can be used to culture the complex microorganisms. Examples of carbon sources of the media include, but are not limited to, glucose, sucrose, dextrin, glycerol, and starch. Examples of nitrogen sources of the media include, but are not limited to, peptone, meat extract, whole milk powder, yeast extract, dried yeast, soybean, ammonium salt, nitrate and other organic and inorganic nitrogenous compounds, and sulfur-containing compounds. One or more inorganic salts may be added to each medium. Examples of such inorganic salts include, but are not limited to, magnesium, manganese, calcium, iron, potassium, sodium, boron, molybdenum, copper, cobalt, and zinc salts. Each medium may further include one or more compounds selected from amino acids, vitamins, nucleic acids, and compounds related thereto.

The microorganisms may be cultured at a temperature of 20° C. to 40° C. or 25° C. to 35° C. for 12 hours to 7 days or 12 hours to 5 days. The complex microorganisms may be in the form of a mixture of culture solutions obtained by individual culture of the respective strains or a mixture of culture solutions obtained by co-culture of the strains. Alternatively, the complex microorganisms may be in the form of a mixture of the strains isolated from the culture solutions.

The method may further include adding an environmentally acceptable carrier to the complex microorganisms or a culture solution, mixture or dried product thereof. The complex microorganisms can be formulated with the carrier to dispose of radioactive waste or to treat soil, groundwater and/or wastewater contaminated with radioactive substances.

Next, the method may include formulating the composition into a liquid or solid preparation. When formulated into a liquid solution, the acceptable carrier may be selected from saline solution, sterilized water, buffered saline, dextrose solution, maltodextrin solution, glycerol, and mixtures thereof that are suitable as nutrients for the complex microorganisms. If necessary, one or more general additives, such as antioxidants, buffer solutions, and bacteriostatic agents may be added to the composition. The composition of the present invention may be formulated into a liquid preparation such as an aqueous solution, suspension or emulsion or a solid preparation such as a powder. In this case, the composition of the present invention may further include one or more additives selected from diluents, dispersants, surfactants, binders, and lubricants.

A further aspect of the present invention relates to a method for transmuting a radioactive substance into a non-radioactive substance, comprising bringing the composition described herein into contact with a radioactive substance.

The contact includes mixing the composition comprising complex microorganisms with the radioactive substance, culturing the composition with the radioactive substance, adding the radioactive substance to the composition, or placing the composition and the radioactive substance in the same reaction system, but is not limited thereto. In one embodiment, the contact may include mixing the composition and the radioactive substance with stirring. The contact may be continued in the temperature range of 20° C. to 40° C. or 25° C. to 35° C. for 12 hours to 3 months, 12 hours to 2 months, 24 hours to 60 days or 36 hours to 56 days.

Advantageous Effects

The complex microorganisms used in the method of the present invention have an outstanding ability to convert radioactive substances into non-radioactive substances and are of great utility in radioactive waste disposal.

In addition, the complex microorganisms are suitable for use in the treatment of soil or groundwater contaminated with radioactive substances or cooling water or wastewater from nuclear power plants.

MODE FOR INVENTION

The present invention will be described in more detail with reference to the following examples. However, these examples are provided for illustrative purposes only and the present invention is not limited thereto.

Example 1

Preparation of Composition Comprising Complex Microorganisms

*Rhodobacter capsulatus* as a photosynthetic bacterial species was cultured in Van Niel's yeast medium supplemented with $K_2HPO_4$ (1 g), $MgSO_4$ (0.5 g), and yeast extract (10 g). The medium was sterilized under high temperature (121° C.) and pressure conditions for 15 min and was allowed to cool to 30° C. Two or three platinum loops of the cultured colonies were inoculated into a solid plate medium under aseptic conditions. Then, the inoculated medium was incubated for 2-3 days with a supply of light from a tungsten lamp while maintaining the temperature at 26° C. under anaerobic conditions, giving a culture solution having a concentration of $1~9\times10^7$ viable cells/mL.

*Coccomyxa viridis, Eliptochloris* sp. and *Stichococcus* sp. *Trebouxia* sp. as green algal species were cultured in Bold's basal medium (BBM) supplemented with a mixture of $KH_2PO_4$ (0.175 g), $CaCl_2.2H_2O$ (0.025 g), $MgSO_4.7H_2O$ (0.075 g), $NaNO_3$ (0.25 g), $K_2HPO_4$ (0.075 g), NaCl (0.025 g), $Na_2EDTA$ (0.1 g), KOH (0.062 g), $FeSO_4.7H_2O$ (0.0498 g), $H_3BO_3$ (0.115 g), $MnCl_2.4H_2O$ (0.00181 g), $ZnSO_4.7H_2O$ (0.000222 g), $NaMoO_4.5H_2O$ (0.00039 g), $CuSO_4.5H_2O$ (0.000079 g), and $Co(NO_3)_2.6H_2O$ (0.0000494 g) in 1 liter of purified water. The medium was sterilized under high temperature (121° C.) and pressure conditions for 15 min and was allowed to cool to 25° C. The cultured green algae were collected by scraping with a cell scraper and inoculated into a solid plate medium. Then, the inoculated medium was incubated for 10 days with a supply of light from a fluorescent lamp (3000 lux) while maintaining the temperature at 20-25° C. under aerobic conditions, giving a culture solution having a concentration of $1.0\times10^5$-$1.0\times10^6$ viable cells/mL.

*Saccharomyces servazzii* KCCM12157P and *Trichosporon loubieri* KCTC10876BP as yeast species and *Phanerochaete chrysosporium* KCCM10725P as a fungal species were cultured in potato dextrose broth (PDB) medium supplemented with potato infusion (200 g) and dextrose (20 g) in 1 liter of purified water. The medium was sterilized under high temperature (121° C.) and pressure conditions for 15 min and was allowed to cool to 30° C. Two or three platinum loops of the cultured yeast were inoculated into a solid plate medium under aseptic conditions. Then, the inoculated medium was incubated for 1 day while maintaining the temperature at 30° C. under aerobic conditions, giving a culture solution having a concentration of $1.0\times10^7$ viable cells/mL.

*Bacillus safensis* KCCM12163P and *Bacillus pumilus* KCCM12165P as radiation-resistant bacterial strains were cultured in Nutrient broth media supplemented with peptone (10 g), beef extract (10 g), and sodium chloride (5 g) in 1 liter of purified water. The medium was sterilized under high temperature (121° C.) and pressure conditions for 15 min and was allowed to cool to 30° C. Two or three platinum loops of the cultured bacterial colonies were inoculated into a solid plate medium under aseptic conditions. Then, the inoculated medium was incubated for 1 day while maintaining the temperature at 30° C. under aerobic conditions, giving a culture solution having a concentration of $1.0\times10^7$-$10^9$ viable cells/mL.

Thereafter, the microorganism culture solutions were combined. The combined culture solution was divided into two groups ("Composition 1" and "Composition 2"), each of which had a concentration of $1\times10^5$-$10^9$ cfu/ml.

Example 2

Preparation of Composition Comprising Complex Microorganisms

A composition comprising complex microorganisms was prepared in the same manner as in Example 1, except that only four of the five culture solutions were used. The four culture solutions were obtained from *Bacillus pumilus* KCCM12165P, *Saccharomyces servazzii* KCCM12157P, *Phanerochaete chrysosporium* KCCM10725P, and *Rhodobacter capsulatus*. The composition was divided into two groups ("Composition 1" and "Composition 2"), each of which had a concentration of $1\times10^7$-$10^9$ cfu/ml.

Comparative Example 1

Preparation of Composition Comprising Single Microorganism Species

A composition was prepared in the same manner as in Example 1, except that only the culture solution of *Bacillus safensis* KCCM12163P was used.

Comparative Example 2

Preparation of Composition Comprising Single Microorganism Species

A composition was prepared in the same manner as in Example 1, except that only the culture solution of *Rhodobacter capsulatus* was used.

Comparative Example 3

Preparation of Composition Comprising Single Microorganism Species

A composition was prepared in the same manner as in Example 1, except that only the culture solution of *Phanerochaete chrysosporium* KCCM10725P was used.

Comparative Example 4

Preparation of Composition Comprising Single Microorganism Species

A composition was prepared in the same manner as in Example 1, except that only the culture solution of *Bacillus pumilus* KCCM12165P was used.

Comparative Example 5

Preparation of Composition Comprising Single Microorganism Species

A composition was prepared in the same manner as in Example 1, except that only the culture solution of *Saccharomyces servazzii* KCCM12157P was used.

Comparative Example 6

Preparation of Composition Comprising Single Microorganism Species

A composition was prepared in the same manner as in Example 1, except that only the culture solution of *Trichosporon loubieri* KCTC10876BP was used.

Comparative Example 7

Preparation of Composition Comprising Single Microorganism Species

A composition was prepared in the same manner as in Example 1, except that only the culture solution of *Stichococcus* sp. was used.

Experimental Example 1

Measurement of Intensities of Radiation from Solutions Containing Cs-137 and the Compositions 100 ml of each of Compositions 1 and 2 prepared in Example 1 and Compositions 1 and 2 prepared in Example 2 was mixed with 400 ml of a liquid sample of Cs-137 (half-life: (30.05±0.08) year, 0.1 M HCl aqueous solution, 50 kBq on Mar. 3, 2018, 0.159 mL). 500 ml of the resulting sample was irradiated with light at 12-h intervals while shaking at ~120 rpm in a shaking incubator at 25° C. Radioactivities from the sample were measured at 24-h intervals. The sample was closed with a lid made of air-permeable, hydrophobic silicon with less water evaporation. The sample including the complex microorganisms and the radioactive isotope was placed on a shaker (DAIHAN Scientific model SHO-2D) and was shaken continuously at ~100 RPM except for ~30 min for radiation intensity measurement. The laboratory temperature was maintained at 21-25° C. without artificial temperature control over the entire experimental period. In the laboratory, fluorescent lamps remained turned on during the experiment and turned off after 6 p.m.

Figure 1:
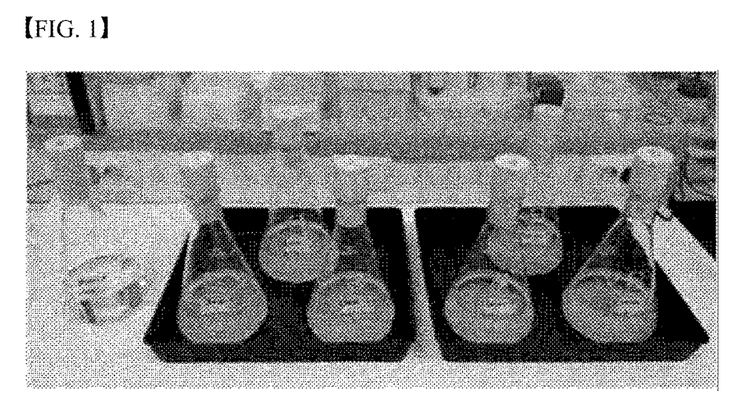
FIG. 1 is a photograph showing samples prepared by adding a radioactive substance (Cs-137) at a concentration of 50,000 becquerels to compositions comprising complex microorganisms in Experimental Example 1.
Figure 2:
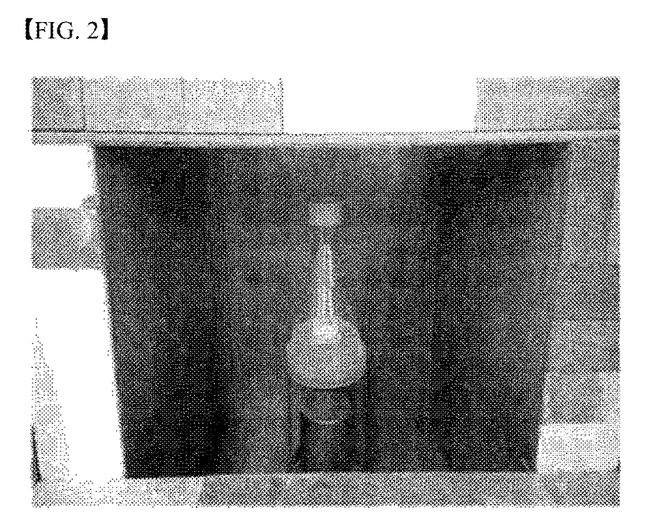
FIG. 2 is a photograph showing a sample holder designed to keep the position of a composition in place relative to detectors such that the intensities of radiation from the composition are observed with time.

Two p-type high-purity Ge detectors with relative efficiencies of ~70% were used to measure radiation intensities. A detection part of each of the Ge detectors is encapsulated in a structure surrounded by a shield to shield gamma rays from the outside. The shield is lined with a 10 cm thick lead plate and a 2 mm thick copper plate. The detector is installed in a vertical cooling system. A sample (or beam source) holder is used to observe the intensities of radiation from the sample with time. The sample holder is designed such that the position of the sample is kept in place relative to the detector. The sample holder is made of an acrylic cylinder and a plate. The sample holder fixes the vertical position of the sample relative to the bottom of the shield. The inner diameter of the cylinder is adapted to the outer diameter of an Erlenmeyer flask containing the sample to fix the horizontal position of the sample. The holder is spaced a distance from the outer periphery of the detector. The detector is fitted into the holder such that the center of the cylinder of the holder coincides with the center of the detector. To this end, the holder is made by cutting an acrylic resin into a doughnut shape. The distances between the upper sides of the detectors and the bottom of the Erlenmeyer flask containing the sample are ~5 mm and ~55 mm (FIG. 2).

Figure 3:
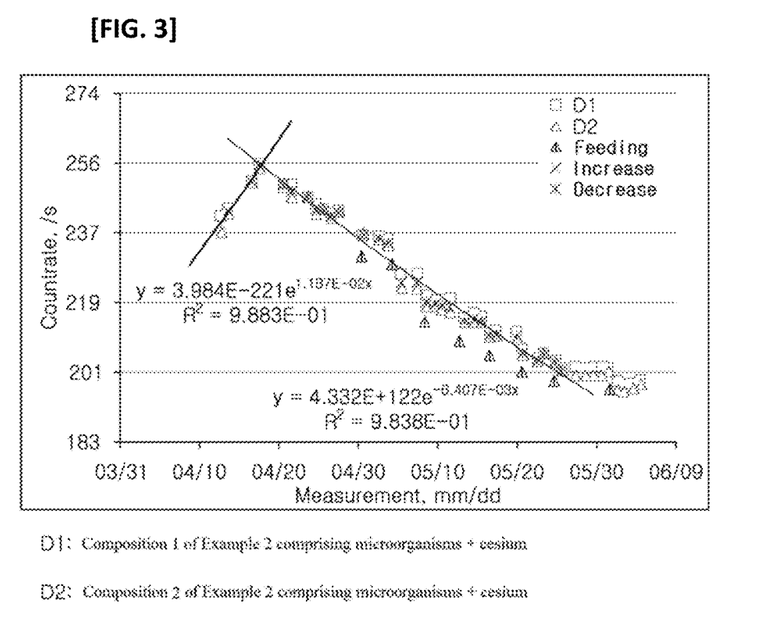
FIG. 3 shows the count rates of gamma rays from $^{137}Cs$ as a radioactive isotope during 49 days of storage of samples prepared by adding the radioactive substance to a composition comprising complex microorganisms in Example 2.
Figure 4:
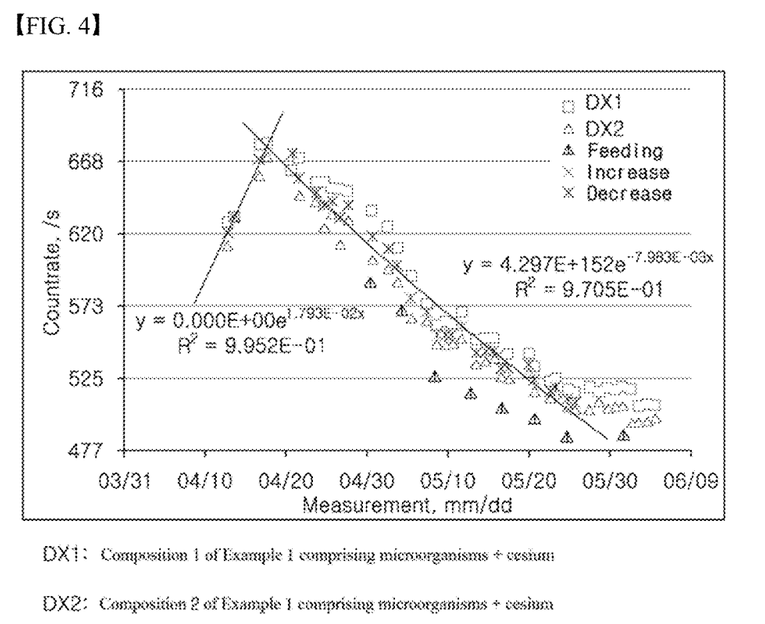
FIG. 4 shows the count rates of gamma rays from $^{137}Cs$ as a radioactive isotope during 49 days of storage of samples prepared by adding the radioactive substance to a composition comprising complex microorganisms in Example 1.

After contact of the complex microorganisms with cesium for a total of 49 days, the count rates of gamma rays per second were measured. The results are shown in FIGS. 3 and 4.

Trend lines were plotted based on the above experimental results. When calculated using the trend lines, the effective initial half-life was estimated to be 39 days from the increased count rates of gamma rays from the radioactive isotope $^{137}C$ with a half-life of 30 years (from April 12 to April 17) and the effective elimination half-life was estimated to be 87 days from the decreased count rates (from April 18 to May 31).

These results support the assumption that the increased count rates of gamma rays at the initial stage are due to the decay of Cs-173 and the decreased count rates of gamma rays are because the microorganisms directly biotransmuted Cs-137 into stable isotopes Ba-137 or Ba-138 without accelerating radioactive decay.

After contact of the composition including only one microorganism with cesium in each of Comparative Examples 1-7, the count rates of gamma rays per second were measured. The results are shown in FIGS. 6-12. No significant decrease in the count rate of gamma rays was observed when only one microorganism was used, unlike when the complex microorganisms were used.

Experimental Example 2

Determination of Transmutation in Solutions Containing Cs-137 and the Compositions To determine whether transmuAtation occurred, cesium was treated with the microorganisms, as in Experimental Example 1. After storage for 60 days, the solutions were sampled. The concentrations of $^{137}Ba$ and $^{138}Ba$ in the samples were analyzed using a high resolution inductively coupled plasma mass spectrometer (HR-ICP-MS). The results are shown in Table 1.

TABLE 1

| No. | Sample name | Ba137 Concentration (µg/L) | RSD (%) | Ba138 Concentration (µg/L) | RSD (%) |
|---|---|---|---|---|---|
| 1 | Control | 0.1741 | 1.64 | 0.124 | 0.50 |
| 2 | D | 17.196 | 0.80 | 17.034 | 0.83 |
| 3 | DX | 23.974 | 0.47 | 23.838 | 0.35 |

D: Composition of Example 2 including the complex microorganisms + average cesium concentration;
DX: Composition of Example 1 including the complex microorganisms + average cesium concentration;
Control: Cesium-containing composition As can be shown from the results in Table 1, the concentrations of $^{137}Ba$ and $^{138}Ba$ in D and DX were ~100-140 times and ~142-194 times higher than those in the control containing only cesium without complex microorganisms. These results demonstrate that the radioactive substance $^{137}Cs$ can be transmuted into non-radioactive substances $^{137}Ba$ and $^{138}Ba$ by the complex microorganisms.

Experimental Example 3

Figure 5:
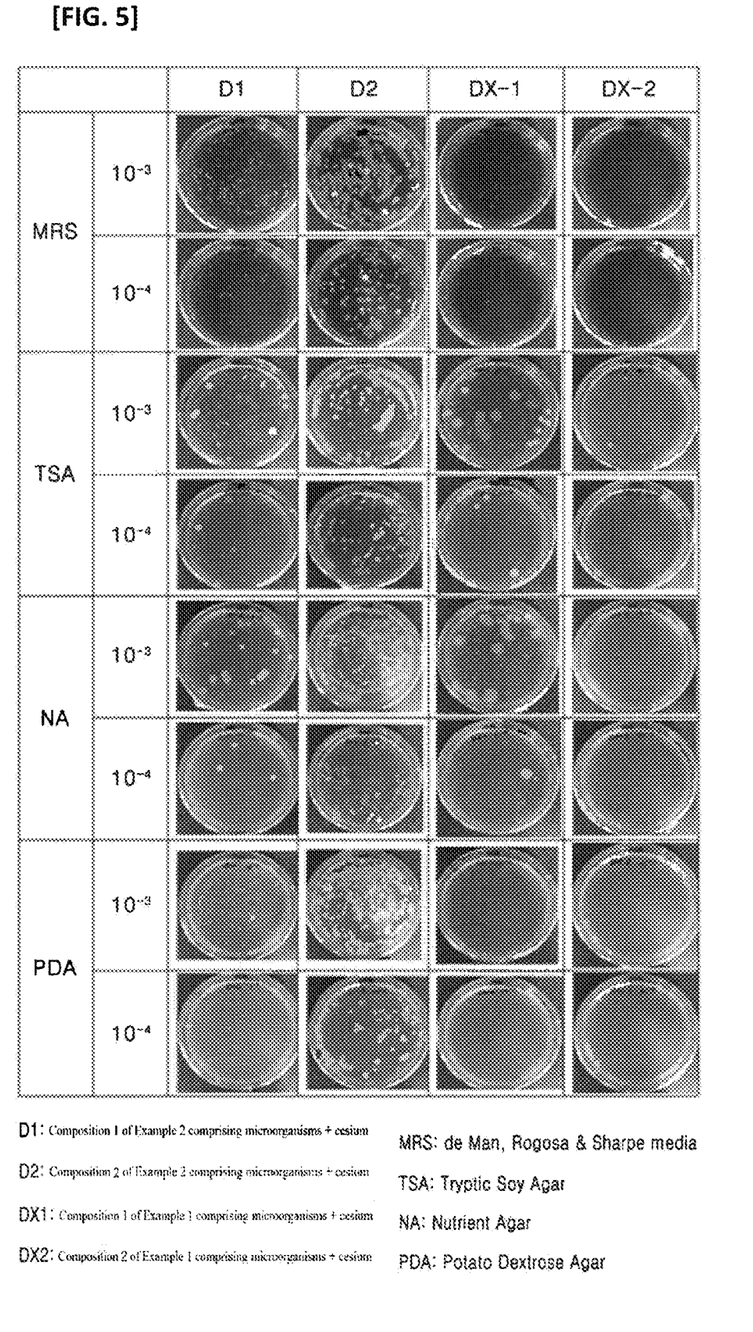
FIG. 5 photographically shows the viability and growth of microorganisms after samples (10 ml each) contaminated with $^{137}Cs$ following radioactivity testing for ~60 days were diluted $10^4$-fold with sterile physiological saline and were added to solid media (NA, MRS, TSA, PDA) supplemented with different nutrients depending on the strain types in order to determine whether or not the complex strains added at the initial stage of testing were viable.
Figure 6:
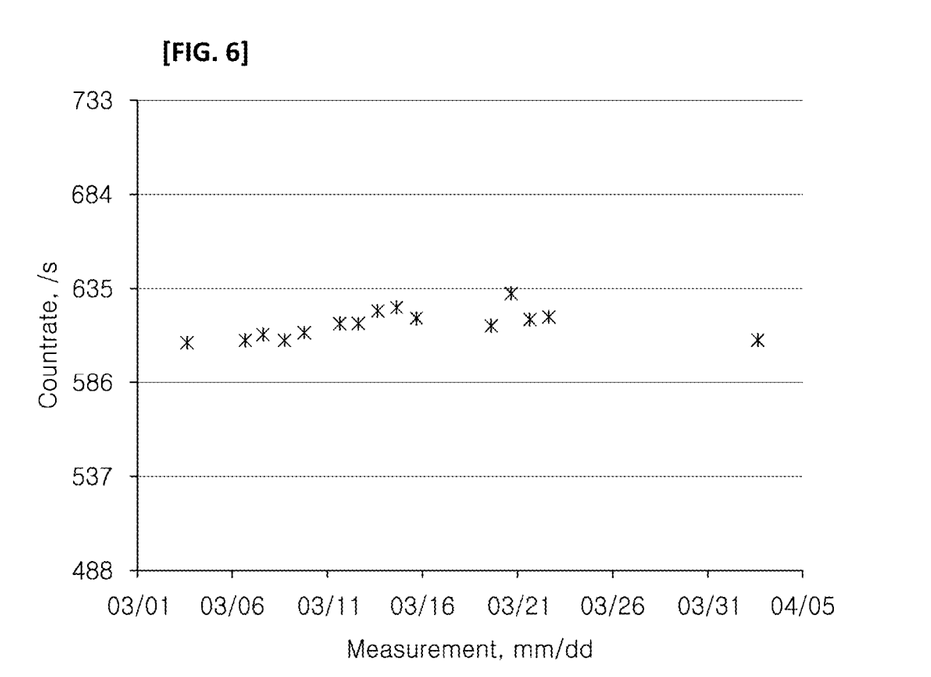
FIG. 6 graphically shows the count rates of gamma rays per second after contact of a composition comprising only one microorganism with cesium in Comparative Example 1.
Figure 7:
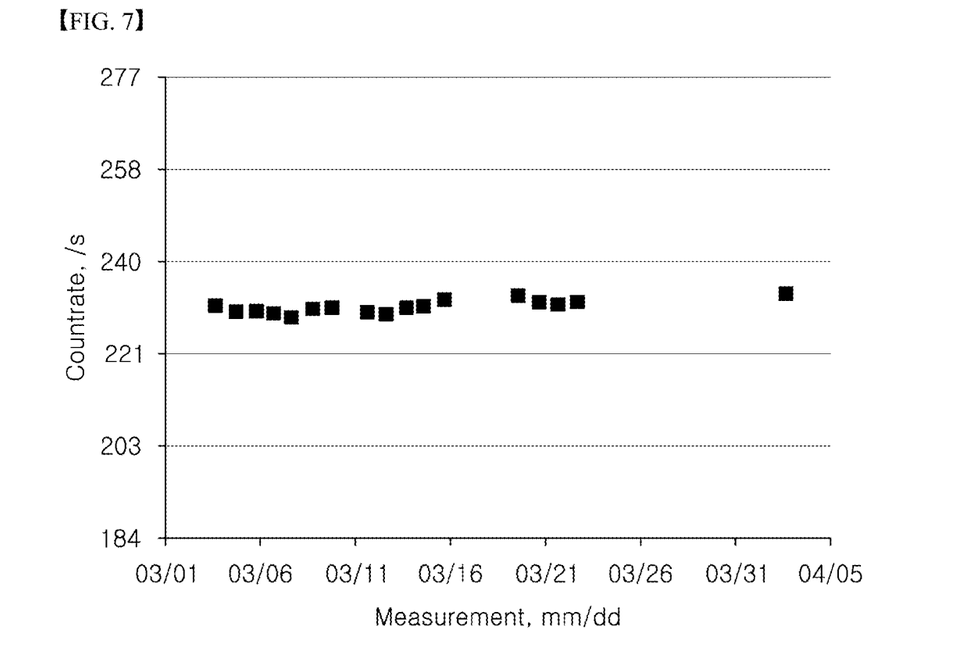
FIG. 7 graphically shows the count rates of gamma rays per second after contact of a composition comprising only one microorganism with cesium in Comparative Example 2.
Figure 8:
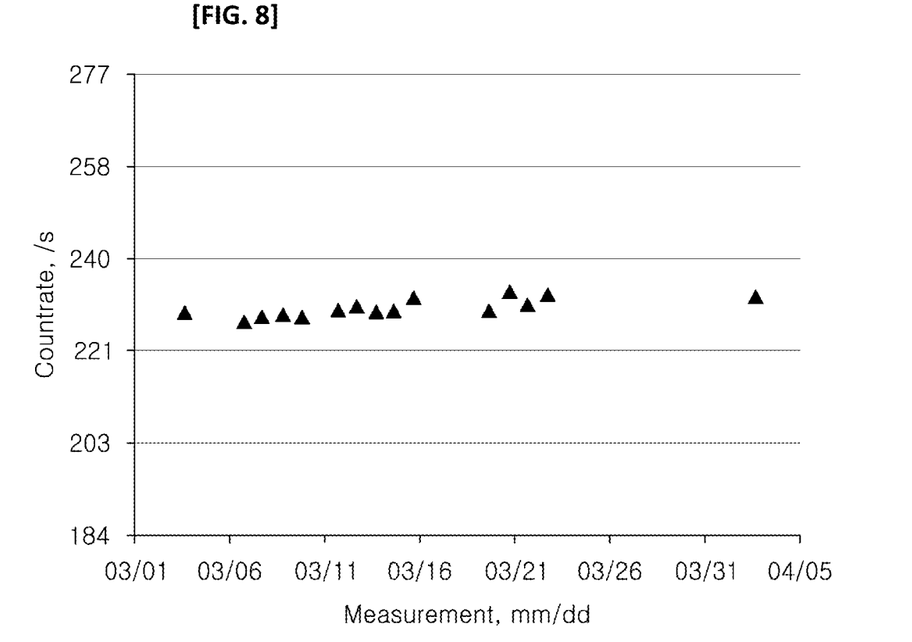
FIG. 8 graphically shows the count rates of gamma rays per second after contact of a composition comprising only one microorganism with cesium in Comparative Example 3.
Figure 9:
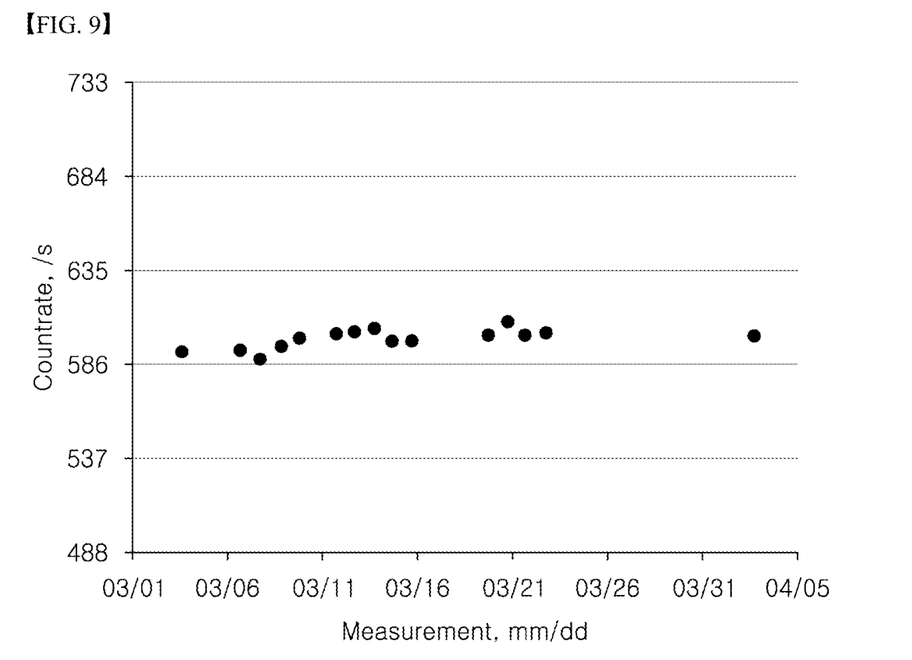
FIG. 9 graphically shows the count rates of gamma rays per second after contact of a composition comprising only one microorganism with cesium in Comparative Example 4.
Figure 10:
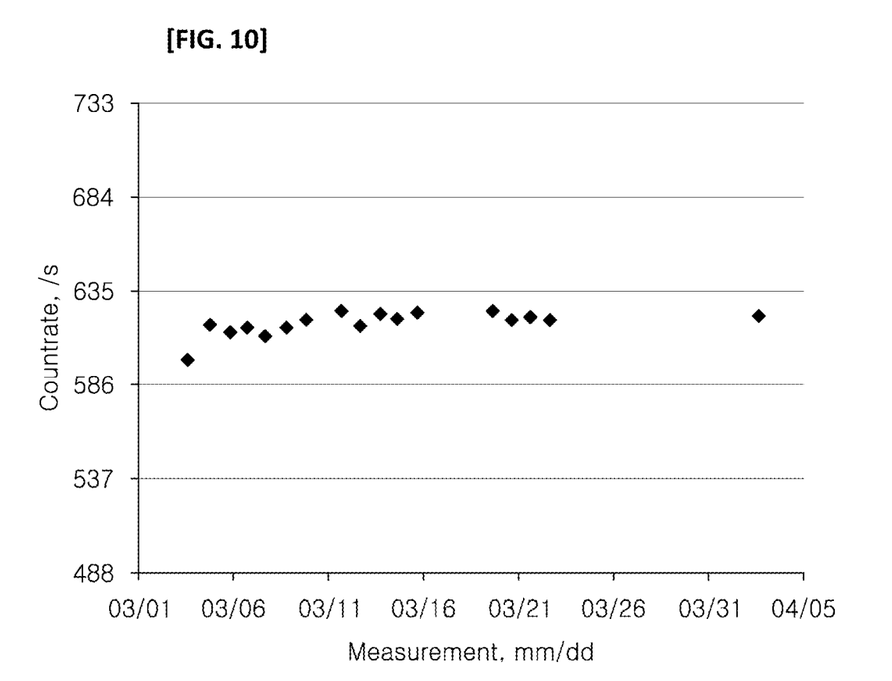
FIG. 10 graphically shows the count rates of gamma rays per second after contact of a composition comprising only one microorganism with cesium in Comparative Example 5.
Figure 11:
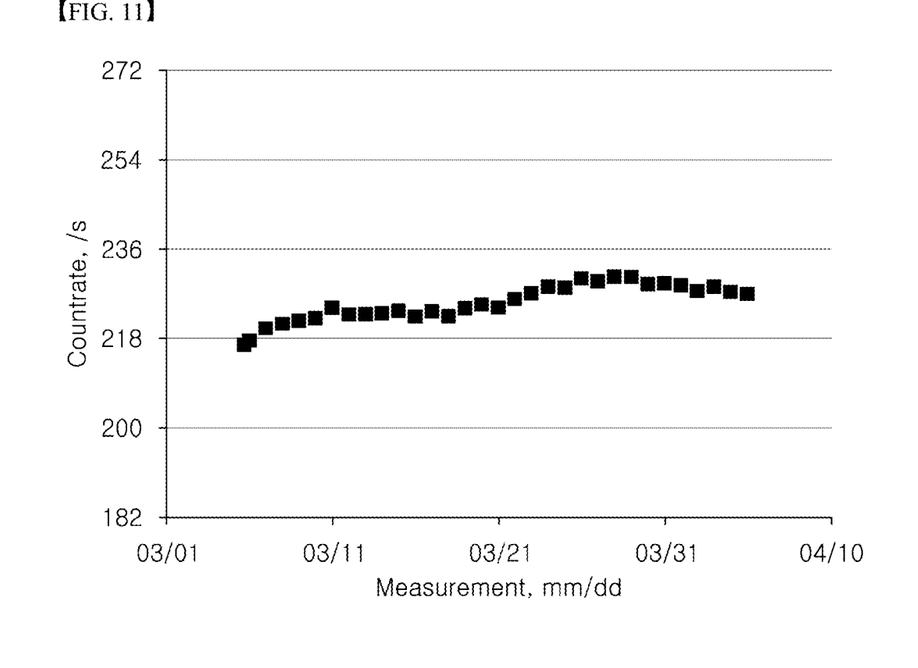
FIG. 11 graphically shows the count rates of gamma rays per second after contact of a composition comprising only one microorganism with cesium in Comparative Example 6.
Figure 12:
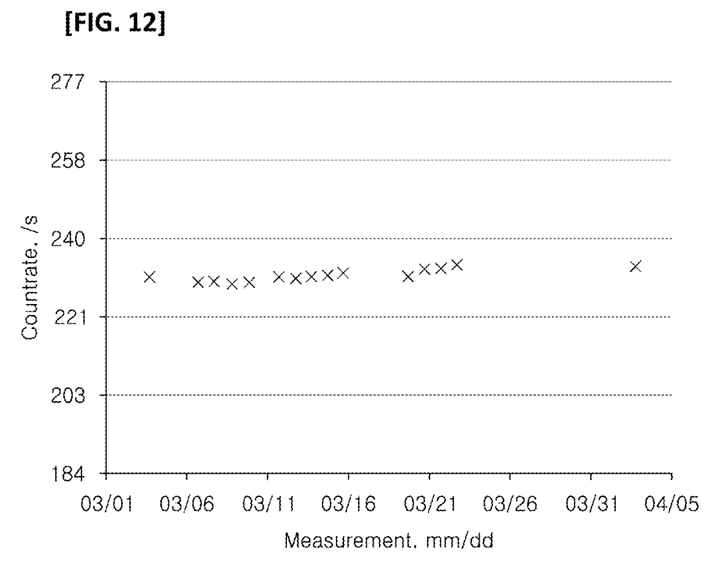
FIG. 12 graphically shows the count rates of gamma rays per second after contact of a composition comprising only one microorganism with cesium in Comparative Example 7.

Determination of Viabilities of the Microorganisms in Solutions Containing Cs-137 and the Compositions To determine the viabilities of the microorganisms, cesium was treated with the microorganisms, as in Experimental Example 1. After storage for 60 days, the solutions were sampled. 10 ml of each of the samples was diluted $10^4$-fold with sterile physiological saline. The viability and growth of the strains in solid media (NA, MRS, TSA, PDA) supplemented with different nutrients depending on the strains were observed (see FIG. 5).

These results concluded that even when contaminated with a high concentration (50,000 becquerels) of radioactive $^{137}$Cs, the complex microorganisms added at the initial stage remained viable at a high concentration (>1×10$^5$ cfu/ml).

The invention claimed is:

1. A composition for transmuting a radioactive substance into a non-radioactive substance, comprising a mixed culture of microorganisms comprising:
a radiation-resistant microorganism selected from the group consisting of *Deinococcus* sp., and *Bacillus* sp.;
a yeast selected from the group consisting of *Cryptococcus* sp., *Saccharomyces* sp. and *Trichosporon* sp.;
a fungus selected from the group consisting of *Irpex* sp. and *Phanerochaete* sp.;
a photosynthetic bacteria species selected from the group consisting of *Rhodobacter* sp.; *Chlorobium* sp., *Chromatium* sp., *Rhodospirillum* sp., and *Rhodopseudomonas* sp.; and
a green algae selected from the group consisting of *Trebouxia* sp., *Stichococcus* sp., *Eliptochloris* sp. and *Coccomyxa* sp;
wherein each of the microorganisms is present at a concentration of 0.5×10$^2$ CFU/ml to 2.5×10$^{10}$ CFU/ml.

2. The composition according to claim 1, wherein the radiation-resistant microorganism is selected from the group consisting of *Deinococcus radiodurans, Bacillus safensis* and *Bacillus pumilus;*
the yeast is selected from the group consisting of *Saccharomyces boulardii, Saccharomyces servazzii, Saccharomyces cerevisiae, Trichosporon cutaneum* and *Trichosporon loubieri;*
the fungus is selected from the group consisting of *Irpex lacteus, Irpex hydnoides, Phanerochaete chrysosporium* and *Phanerochaete sordida;*
the photosynthetic bacterial species is selected from the group consisting of *Rhodobacter sphaeroides* and *Rhodobacter capsulatus*; and
the green algae is selected from the group consisting of *Coccomyxa viridis* and *Stichococcus* sp.

3. The composition according to claim 1, wherein the microorganisms are present in a total amount of 0.05% by weight to 60% by weight, based on the weight of the composition.

4. The composition according to claim 1, wherein the radioactive substance is cesium (Cs), uranium, iodine, strontium, iridium, radium or plutonium.

5. The composition according to claim 1, further comprising an environmentally acceptable carrier.

6. The composition according to claim 1, wherein the composition is used to dispose of radioactive waste or to treat soil, groundwater or wastewater, contaminated with radioactive substances.

7. A method for preparing the composition for transmuting a radioactive substance into a non-radioactive substance as set forth in claim 1, the method comprising:
culturing the radiation-resistant microorganisms, the yeast, the fungi, the photosynthetic bacteria, and the green algae in culture medium individually or at least partially together; and
mixing the cultured microorganisms to form the composition.

8. The method according to claim 7, wherein the microorganisms are cultured at a temperature of 20° C. to 40° C. for 12 hours to 7 days.

9. The method according to claim 7, wherein the cultured microorganisms are mixed with stirring.

* * * * *